(12) United States Patent
Chen et al.

(10) Patent No.: US 8,999,294 B2
(45) Date of Patent: Apr. 7, 2015

(54) NANOPARTICLES FOR USE IN TUMOR DIAGNOSIS AND THERAPY

(75) Inventors: Wei Chen, Arlington, TX (US); Yuebin Li, Wuhan (CN)

(73) Assignee: The Board of Regents of the University of Texas System, Austin, TX (US)

( * ) Notice: Subject to any disclaimer, the term of this patent is extended or adjusted under 35 U.S.C. 154(b) by 163 days.

(21) Appl. No.: 13/166,672

(22) Filed: Jun. 22, 2011

(65) Prior Publication Data

US 2012/0190975 A1 Jul. 26, 2012

Related U.S. Application Data

(60) Provisional application No. 61/357,705, filed on Jun. 23, 2010.

(51) Int. Cl.
| | | |
|---|---|---|
| *A61B 5/055* | (2006.01) | |
| *A61K 9/14* | (2006.01) | |
| *A01N 59/20* | (2006.01) | |
| *C01G 3/12* | (2006.01) | |
| *A61K 41/00* | (2006.01) | |
| *A61K 49/04* | (2006.01) | |
| *B82Y 5/00* | (2011.01) | |
| *B82Y 15/00* | (2011.01) | |
| *B82Y 30/00* | (2011.01) | |
| *C01B 19/00* | (2006.01) | |
| *C01G 3/02* | (2006.01) | |
| *B82Y 40/00* | (2011.01) | |

(52) U.S. Cl.
CPC .............. *C01G 3/12* (2013.01); *A61K 41/0052* (2013.01); *A61K 49/0485* (2013.01); *B82Y 5/00* (2013.01); *B82Y 15/00* (2013.01); *B82Y 30/00* (2013.01); *C01B 19/007* (2013.01); *C01G 3/02* (2013.01); *B82Y 40/00* (2013.01); *C01P 2002/54* (2013.01); *C01P 2002/72* (2013.01); *C01P 2002/82* (2013.01); *C01P 2002/84* (2013.01); *C01P 2004/04* (2013.01); *C01P 2004/64* (2013.01)

(58) Field of Classification Search
CPC ... A61N 1/403; A61K 41/0052; A61K 49/00; A61K 9/14
See application file for complete search history.

(56) References Cited

U.S. PATENT DOCUMENTS 6,689,338 B2 * 2/2004 Kotov .......................... 424/1.69
2002/0103517 A1 * 8/2002 West et al. ...................... 607/88

OTHER PUBLICATIONS

Roy, P., et al., "Low-temperature synthesis of CuS nanorods by simple wet chemical method", 2006, Mater. Lett., pp. 1693-1697.*
Grozdanov, I., et al., "Optical and Electrical Properties of Copper Sulfide Films of Variable Composition", 1995, J. Solid State Chem, pp. 469-475.*
Wu, Y., et al., "Synthesis and Photovoltaic Application of Copper(I) Sulfide Nanocrystals", 2008, Nano Letters, pp. 2551-2555.*
Qin, A. et al., "Formation of Various Morphologies of Covellite Copper Sulfide Submicron Crystals by a Hydrothermal Method without Surfactant", 2005, Crystal Growth Design, pp. 855-860.*
Toshihiro Kuzuya et al., Electrochimica Acta, vol. 53, Issue 1, Nov. 20, 2007, pp. 213-217.
Hongliang Zhu et al., Microporous and Mesoporous Materials, vol. 80, Issue 1-3, May 2, 2005, pp. 153-156.
Haolan Xu et al., Materials Letters, vol. 60, Issues 17-18, Aug. 2006, pp. 2203-2206.
Chunyan Wu et al., Large scale synthesis of uniform CuS nanotubes in ethylene glycol by a sacrificial templating method under mild conditions, J. Mater. Chem., 2006, 16, pp. 3326-3331.
Weimin Du et al., Chemistry—A European Journal, vol. 13, Issue 11, pp. 3241-3247, Apr. 5, 2007.
Colin M. Hessel et al., Nano Lett., 2011, 11 (6), pp. 2560-2566.
Min Zhou et al., J. Am. Chem. Soc., 2010, 132 (43), pp. 15351-15358.
Jonathan J. Brege et al., Nano Lett., 2009, 9 (6), pp. 2239-2242.
Wei Lu et al., Clin Cancer Res Feb. 1, 2009 15; pp. 876-886.

* cited by examiner

*Primary Examiner* — Michael G Hartley
*Assistant Examiner* — Lance Rider
(74) *Attorney, Agent, or Firm* — Winstead PC (57) ABSTRACT

The present invention relates to diagnostic and therapeutic nanoparticles. More particularly, the present invention relates to creating a copper (Cu)-based nanoparticle and a method for making the same. The Cu-based nanoparticles can further be incorporated with additional therapeutic or diagnostic compounds and used for the diagnosis and treatment of tumors.

2 Claims, 9 Drawing Sheets

NANOPARTICLES FOR USE IN TUMOR DIAGNOSIS AND THERAPY

CROSS-REFERENCES TO RELATED APPLICATIONS

This application claims the benefit of U.S. Provisional Patent Application Ser. No. 61/357,705, filed Jun. 23, 2010, and incorporated herein by reference in its entirety.

BACKGROUND OF THE INVENTION

1. Field of the Invention

The present invention relates to diagnostic and therapeutic nanoparticles. More particularly, the present invention relates to creating a copper (Cu)-based nanoparticle and a method for making the same. The Cu-based nanoparticles can further be incorporated with additional therapeutic or diagnostic agents. The nanoparticles of the present invention have the capability to absorb near infrared wavelength light to act as a therapeutic agent by generating heat energy effective for cell ablation.

2. Description of the Prior Art

Cancer is a group of diseases characterized by uncontrolled growth and spread of abnormal cells. If the spread is not controlled, it can result in death. Cancer is caused by both external factors (tobacco, infectious organisms, chemicals, and radiation) and internal factors (inherited mutations, hormones, immune conditions, and mutations that occur from metabolism). Cancer is treated with surgery, radiation, chemotherapy, hormone therapy, biological therapy, and targeted therapy. In 2011, about 571,950 Americans are expected to die of cancer, more than 1,500 people a day. Cancer is the second most common cause of death in the US, exceeded only by heart disease. In the US, cancer accounts for nearly 1 of every 4 deaths. (Cancer Facts and Figures 2011, American Cancer Society).

Cancer of the liver affects greater than half a million patients worldwide. U.S. liver-related cancer deaths account for 4% of all cancers or about 20,000 deaths annually. Currently available minimally invasive procedures have the tendency to leave a population of malignant cells intact, allowing for recurrence of the tumor and accounts for the varied recurrence rates seen.

Similarly, the rate of prostate cancer in men was 33% of all cancers in the U.S. in 2004. Prostate cancer easily metastasizes, increasing the chance of death if not caught early. In the current stage of detection through prostate specific antigen (PSA), at least 25% of U.S. men tested as present with metastases to the bone. These men have a 90% risk of death within five years. The high mortality rates of these cancers after metastasis, is a significant health risk.

Nanoparticles can be efficiently delivered into cancerous tissue, such as tumors, via a property inherent of fast growing neoplasias called Enhanced Permeability and Retention ("EPR"). This property is marked by "leaky vasculature" within tumors, allowing extravasation and retention of macromolecules or nanoscale particles. Silica core/gold nanoshells (composite nanoparticles) which have tunable plasmon resonance in the near infrared ("NIR") range have been used to induce sufficient thermal damage after accumulation via this mechanism leading to tumor reduction and increased survival. Using light based imaging techniques (optical coherence tomography or OCT) these nanoparticles have been used as a theranostic (i.e., combined diagnostic and therapeutic) agent in a single nanoshell formulation. Though these particles may provide effective diagnostic capabilities for shallow (<5 mm) tumors they are unsuitable as a good diagnostic approach where tumors may be deeply situated.

However, in addition to being expensive, the size of the gold nanoparticles smaller than 10 nm are not easy to make. Special structures like core-shell nanostructures and hollow gold nanorods are required in order for gold nanostructures to have absorption in the NIR ranges, and the recipes for making these nanostructures are very complicated. Thus, a need exists for a therapeutic agent having strong absorption in the NIR region, small size, low cost of production relative to gold particles, and low cytotoxicity.

Photothermal Ablation (PTA) of cancer is the use of heat between 41° C. and 45° C. to damage cancer cells. PTA is an effective modality for cancer treatment that has been investigated extensively. The beauty of PTA is its duality for targeting—that is the targeting of the agents and the light that used for activation. The duality of targeting can effectively reduce the side effects and the risk of damage to the surrounding healthy tissue. A significant obstacle to successful PTA is that healthy tissues can also absorb energies and could be damaged by heat. The application of functional nanoparticles may overcome this limitation because nanoparticles can be selectively directed to the cancer cells. Gold nanostructures (nanoparticles, nanoshells, and hollow nanospheres) have been investigated extensively for photothermal ablation therapy induced by NIR light, hence the term photothermal ablation therapy. As a new type of agents for photothermal treatment of cancer, CuS nanoparticles have many advantages. The most favorable features are the low-costs, simple and easy for preparation and small size for targeting.

SUMMARY OF THE INVENTION

The nanoparticle of the claimed invention will benefit patients with many forms of cancer. The benefits will include better ability to diagnose primary as well as metastatic cancer events due to the nanoparticle's small size, thus allowing accumulation within even small tumors. Once located via computed tomography (CT) scan, these nanoparticles can be activated by the use of directed NIR light to optically heat the nanoparticles. This will allow heating of the nanoparticles for immediate killing of cancerous cells containing the nanoparticles, where the heating causes an increase in temperature of 12-18° C. above body temperature. As EPR as well as active targeting with cancer cell specific binding ligands causes nanoparticles to accumulate in tumor cells, normal cells will remain unharmed.

The CuS nanoparticles of the present invention have a broad absorption peak at around 900 nm. Furthermore, the interaction of CuS nanoparticles with NIR light can generate heat that can be harnessed for PTA of cancer cells.

An embodiment of the invention is directed to a nanoparticle comprising copper sulfide, said nanoparticle having a diameter of less than about 3 nm and an absorbance peak between about 700-1100 nm.

A further embodiment of the invention is directed to a method for the removal of cancer cells, the method comprising comprising the steps of: (a) providing optically heatable nanoparticles having diameters of about 3 nm and improved contrast functionality with X-ray and CT imaging; (b) delivering the nanoparticles to a specific target; (c) imaging the target using at least one of X-ray and CT imaging; (d) optically heating the nanoparticles located at the specific target, whereby optically heating the nanoparticles results in at least one of: (1) thermal ablation of at least a portion of the specific target; (2) release of a diagnostic agent incorporated within the nanoparticles; (3) release of a therapeutic agent incorporated within the nanoparticles.

An additional embodiment of the invention is directed to a method for forming CuS nanoparticles, the method comprising the steps of: preparing a solution comprising a copper salt and thioglycolic acid in water; adjusting the pH of the solution using sodium hydroxide; adding a solution of thioacetamide to form a mixture; and heating the mixture to form nanoparticles.

BRIEF DESCRIPTION OF THE DRAWINGS

FIG. 5 shows the results of cell viability after NIR irradiation: (A) HeLa cells were treated with different concentrations of CuS nanoparticles and 808-nm NIR light at 24 W/cm$^2$ for 5 min. After treatment with nanoparticles at a concentration of 384 µM CuS plus NIR laser, most cells were dead in the zone of exposure (circled area). In contrast, after treatments with NIR laser alone, nanoparticles alone, or nanoparticles at concentrations of 192 µM CuS followed by NIR laser, cells retained normal morphology, and few dead cells were observed; (B) When irradiated with an NIR laser at a higher power (40 W/cm$^2$ for 5 min), cell death was observed at a lower concentration of 192 µM CuS, and the cell death expanded beyond the zone of irradiation when the nanoparticle concentration was increased to 384 µM CuS. Viable cells were stained green with calcein, dead cells were stained red with EthD-1. Bar=200 µm; NP, nanoparticles

DETAILED DESCRIPTION OF EXEMPLARY EMBODIMENTS

In an embodiment of the invention, a nanoparticle comprises a CuS nanoparticle. In some embodiments, the nanoparticle further includes a CT contrast agent and/or a therapeutic agent or diagnostic agent. The CT contrast agent and/or a therapeutic agent or diagnostic agent may be incorporated in a coating on the surface of the nanoparticle. The term nanoparticle is used herein to collectively refer to a nanoparticle and any coating, agent, or other material attached thereto.

In an embodiment of the invention the nanoparticles are around 3 nm in diameter. The nanoparticles of the invention exhibit strong absorption in the NIR region. Irradiation by a NIR laser beam elevates the temperature of aqueous solutions of nanoparticles as a function of exposure time and nanoparticle concentration.

In certain embodiments of the invention, the nanoparticles mediate photothermal destruction of cancer cells in a laser dose- and nanoparticle concentration-dependent manner. Furthermore, the nanoparticles of the invention displayed minimal cytotoxic effects.

An embodiment of the invention is directed to photothermal ablation (PTA) therapy, which uses light to produce heat to damage cancer cells by raising temperature between 41° C. to 45° C. CuS nanoparticles display a broad absorption between 700 and 1100 nm peaking at around 900 nm, thus can serve as tool in the PTA therapy of cancer cells.

In certain embodiment of the invention, the nanoparticles may modified by encapsulating the nanoparticles into poly(lactide) (PLA) or poly(lactide-co-glycolide) (PLGA) microspheres. These encapsulated nanoparticles have comparable efficacy to non-encapsulated nanoparticles and possess improved cytotoxicity properties.

In other embodiments of the invention, the nanoparticles may be encapsulated into a carrier such as polymers, liposomes or inorganic porous vehicles such as zeolites, MCM-41 or silica.

In certain embodiments of the invention, the nanoparticles of the invention may be used for the diagnosis and treatment of internal cancers such as breast and prostate cancers and deep tissue tumors.

In other embodiments, the nanoparticles of the invention may be formulated in the form of gels for topical application to skin cancers or tumors on the surface of a human or animal subject. The topical formulations of the nanoparticles are also useful in the treatment of diseases such as eczema and psoriasis.

Other applications of the invention include treatment of bacterial infections and viral diseases using compositions comprising nanoparticles of the invention.

An embodiment of the claimed invention is directed to a nanoparticle comprising copper sulfide. In certain embodiments of the invention, the nanoparticles have the formula Cu$_x$S$_y$ (0<x<1, 0<y<1). Additionally, the copper present in the nanoparticles of the invention includes all isotopes of copper found in nature.

In other embodiments of the invention, the nanoparticles have the formula CuX, where X=S, Se, Te or O. Certain of the nanoparticles of the invention are further complexed with one or more additional metals that function as dopants. An embodiment of the invention includes nanoparticles having the structure CuX:Y, where X=S, Se, Te and O; and Y=Ag, Zn, Fe, Ni, Pb, Eu, Yb, Er, where Y is a dopant of any ions that have magnetism or luminescence. The doping into CuX nanocrystals enables the applications of CuX nanoparticles simultaneously for cancer treatment and observations. The observations can be possible either by luminescence imaging or magnetic imaging such nuclear magnetic resonance or electron spin or paramagnetic resonance (ERS or EPR) imaging.

In another embodiment, the claimed invention is directed to a process for making a nanoparticle comprising the steps of: (a) providing a copper source; (b) providing a sulfide source; and (c) combining the copper source and the sulfide source for self-assembly of a nanoparticle comprising copper sulfide.

An alternate embodiment may further comprise step (d): incorporating at least one of a therapeutic agent, a diagnostic agent, and a contrast agent into the nanoparticle or coating the nanoparticle with at least one of a therapeutic agent, a diagnostic agent, and a contrast agent. The at least one of a therapeutic agent, a diagnostic agent, and a contrast agent may be an antibody, dye or a pharmaceutical. In certain embodiments, nanoparticles of the invention are coated with organic dyes having luminescence which facilitates their use for disease treatment and observations at the same time.

In another embodiment, the claimed invention is a method for using nanoparticles comprising the steps of: (a) providing optically heatable nanoparticles having diameters of about 3 nm and improved contrast functionality with X-ray and CT imaging; (b) delivering the nanoparticles to a specific target; (c) imaging the target using at least one of X-ray and CT imaging; (d) optically heating or exciting the nanoparticles located at the specific tissue, whereby optically heating the nanoparticles results in at least one of: (1) thermal ablation of at least a portion of the specific target; (2) release of a diagnostic agent incorporated within the nanoparticles; (3) release of a therapeutic agent incorporated within the nanoparticles. In this embodiment, each of the nanoparticles may be comprised of a nanoparticle comprising copper sulfide, and a coating assembled on the nanoparticle. In this embodiment, a contrast agent may be incorporated within the coating and the contrast agent may not be released upon optically heating the hybrid nanoparticle. In this embodiment, the specific target may be a cancerous tissue.

In a further embodiment, the present invention is a method for delivering a therapeutic or diagnostic agent to a specific target comprising the steps of: (a.) providing optically heatable nanoparticles comprised of: (1) a nanoparticle comprising copper sulfide; (2) a coating assembled on the nanoparticle; (3) at least one agent from the group consisting of a therapeutic agent and a diagnostic agent, the agent releasably incorporated within the coating; (b) delivering the hybrid nanoparticles to a specific target; (c) optically heating the nanoparticles located at the specific target, whereby optically heating the hybrid nanoparticles results in release of the at least one agent.

In a further embodiment, the present invention is directed to a method of using CuX nanoparticles doped with Cu ions or other alkaline or rare earth ions, such that photothermal treatment and imaging of cancer can be conducted simultaneously.

WORKING EXAMPLES

Materials

Thioglycolic acid (TGA), $CuCl_2 \cdot 2H_2O$, and thioacetamide were purchased from Sigma-Aldrich (St. Louis, Mo.). RPMI-1640 culture medium, calcein AM and EthD-1 LIVE/DEAD® viability kit were obtained from Invitrogen (Eugene, Oreg.). Gold nanoparticles (20 nm) were prepared by adding 5 mL of sodium citrate (25 mM) into a boiling aqueous solution of $HAuCl_4$ (0.25 mM). The mixture was stirred until the solution turned into wine red color, indicating the completion of the reaction. Human cervix adenocarcinoma HeLa cells and human embryonic kidney 293 cells (HEK293) were obtained from American Type Culture Collection (Manassas, Va.).

Nanoparticle Synthesis and Characterization

Thioglycolic acid (TGA)-stabilized CuS nanoparticles were synthesized as follows: 0.017048 g of $CuCl_2\text{-}2H_2O$ (0.1 mmol) was dissolved in 100 ml of distilled water, 0.2 mmol of TGA (approximately 14.2 µL) was added into the solution under constant stirring, and the pH was adjusted to 9.0 by drop-wise addition of a 1 M solution of NaOH. The solution was placed in a three-necked flask fitted with a septum and valves and was degassed by argon bubbling for 20 min. A solution of thioacetamide (8.0 mg, 0.1 mmol) in distilled water (20 ml) was added, and the solution was heated at 50° C. for 2 h to promote nanoparticle growth.

The crystalline structure, size, and shape of the nanoparticles were observed by XRD and HRTEM. XRD was measured using a Siemens Kristalloflex 810 D-500 x-ray diffractometer (Karslruhe, Germany) under an operating mode of 40 kV and 30 mA, with $\lambda$=1.5406 Angstrom radiation. The nanoparticles in solution were placed onto holey carbon-covered copper grids for HRTEM observation. The HRTEM images of the particles were obtained with a JEOL JEM-2100 electron microscope (Tokyo, Japan) with accelerating voltage of 200 kV. The absorption spectra were recorded using a Shimadzu UV-2450 UV-Vis spectrophotometer (Kyoto, Japan).

Photothermal Effect in Aqueous Solution

The laser was a continuous wave GCSLX-05-1600m-1 fiber-coupled diode laser (China Daheng Group, Beijing, China) with a center wavelength of 808±10 nm. A 5-m, 600-µm core BioTex LCM-001 optical fiber (Houston, Tex.) was used to transfer laser light from the laser unit to the target. This fiber had a lens mounting at the output that allowed the laser spot size to be changed by changing the distance from the output to the target. The output power was independently calibrated using a handheld optical power meter (Newport model 840-C, Irvine, Calif.) and was found to be 1.5 W for a spot diameter of 1.3 mm (24 W/cm$^2$) and a 2-amp supply current. For measuring temperature change mediated by CuS nanoparticles, 808-nm NIR laser light was delivered through a quartz cuvette containing the nanoparticles (100 µL). A thermocouple was inserted into the solution perpendicular to the path of the laser light. The temperature was measured over a period of 15 min. Water was used as a control.

Laser or laser diodes or a lamp with wavelengths from 600-1150 nm can be used for the same purpose of cancer ablation in combination with the nanoparticles in this invention. Laser with longer wavelengths, such as 980 nm, a lower power (3-10 W/cm$^2$) is needed for the same effects.

In Vitro Photothermal Ablation of Cancer Cells with CuS Nanoparticles

HeLa cells were seeded onto a 96-well plate at a density of 10,000 cells per well 1 day before the experiment. Cells were washed three times with Hanks balanced salt solution (HBSS, Sigma-Aldrich) followed by incubation with CuS nanoparticles (0, 96, 192, or 384 µM equivalent CuS) at 37° C. for 2 h. After incubation was completed, the culture media with nanoparticles were removed and the cells re-supplied with fresh phenol red-free RPMI-1640 (Invitrogen, Carlsbad, Calif.). Cells were irradiated with an NIR laser centered at 808 nm at an output power of 0, 24, or 40 W/cm$^2$ for 5 min or 254 W/cm$^2$ for 3 min (Diomed, Andover, Mass.). The diode laser was coupled to a 1-m, 2-mm core fiber, which delivered a circular laser beam of 2 mm in diameter, covering the central area of the microplate well. Power calibration was done automatically. After laser irradiation, cells were re-supplied with RPMI-1640 containing 10% fetal bovine serum and incubated at 37° C. for 24 h. The cells were then washed with HBSS and stained with calcein AM for visualization of live cells and with EthD-1 for visualization of dead cells, according to the manufacturer's suggested protocol (Invitrogen). Cells were examined under a Zeiss Axio Observer.Z1 fluorescence microscope (Carl Zeiss Microlmaging GmbH, Gottingen, Germany). The fluorescent intensity of each well was measured using a TECAN microplate reader with Magellan software (Mannedorf, Switzerland). The percentage of viable cells in each well was calculated according to the manufacturer's protocol. Each experiment was performed in triplicate. Differences in viability between each treatment and the control (i.e., no laser, no nanoparticles) were analyzed using Student's t-test, with $p<0.05$ considered to be statistically significant.

Cytotoxicity

Cell viability was measured using the tetrazolium salt (WST-1) assay kit (Takara Bio, Inc., Shiga, Japan) after 48 h of continuous exposure to the CuS or 20-nm gold nanoparticles. WST-1 (4-[3-(4-iodophenyl)-2-(4-nitrophenyl)-2H-5-tetrazolio]-1,3-benzene disulfonate) works similarly to MTT by reacting with the mitochondrial succinate-tetrazolium reductase forming the formazan dye. The WST-1 reagent produces a water-soluble formazan rather than the water-insoluble product of the MTT assay. Exponentially growing HEK293 cells were dispensed into a 96-well flat bottom plate ($10^3$ cells/well, 100 μL). After allowing 24 h for cell attachment, each nanoparticle solution or aqueous solution of $CuCl_2$ was diluted appropriately in fresh media and added to the microwells (100 μL), 3 wells per concentration. Cell viability was determined by the addition of WST-1 solution (20 μL/well). The plate was incubated for an additional 2 h at 37° C. and 5% $CO_2$, allowing viable cells to convert the WST-1 into a colored dye by using mitochondrial dehydrogenase enzymes. The soluble salt was then released into the media. Absorbance at 430 nm was measured against a background control as blank using a microtiter plate reader (Molecular devices, Sunnyvale, Calif.). Data were presented as mean absorbance±standard deviation.

Figure 1:
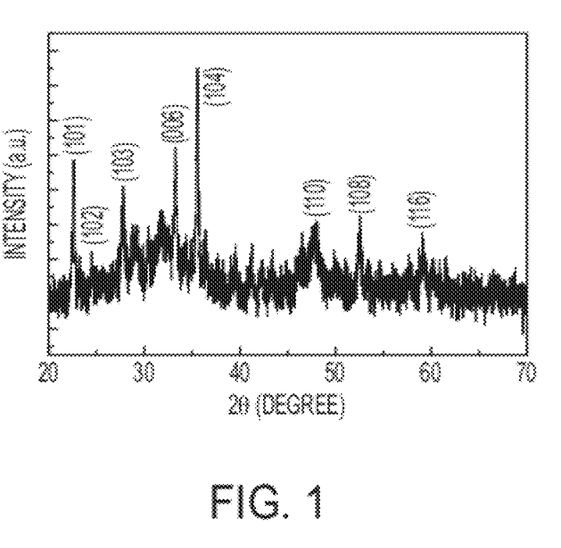
FIG. 1 shows an X-ray diffraction pattern of CuS nanoparticles.
Figure 2:
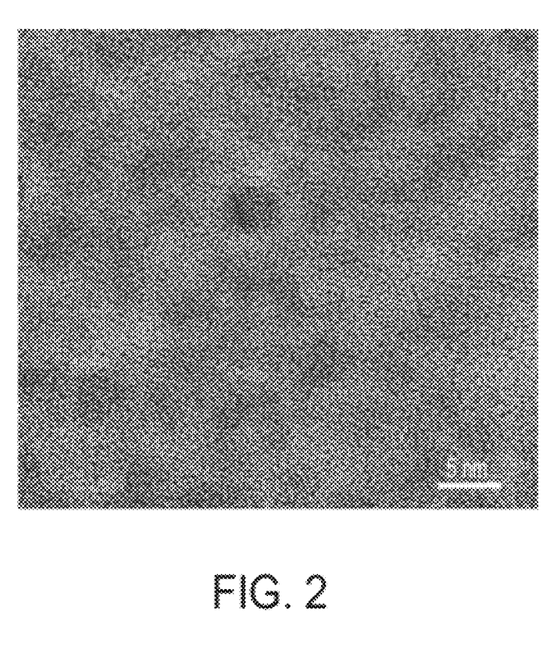
FIG. 2 shows a high-resolution transmission electron microscope image of CuS nanoparticles.

In accordance with an embodiment of the invention, CuS nanoparticles are synthesized in aqueous solution by reacting $CuCl_2$ and thioacetamide in the presence of thioglycolic acid (TGA) at pH 9. TGA serves to stabilize the resulting CuS nanoparticles. FIG. 1 shows the x-ray diffraction (XRD) pattern of CuS nanoparticle powder deposited from the aqueous solution, which is in agreement with that of the standard powder diffraction pattern of CuS with a hexagonal structure. The diffraction lines are indexed as labeled in FIG. 1 for the hexagonal phase of CuS. The broadening of the diffraction peaks indicates the formation of nanoscale particles. No obvious impurity peaks were observed, indicating the acquirement of high-quality covellite CuS. FIG. 2 shows the high-resolution transmission electron microscope (HRTEM) images of CuS nanoparticles. The average size was about 3 nm with a uniform size distribution. Assuming a density of 4.6 g/cm$^3$, each CuS nanoparticle is estimated to contain approximately 3,260 CuS "molecules". The nanoparticles had a hexagonal structure and the crystal lattice fringes from the [102] and [103] lattice planes could be observed. The lattice spacing of the [102] plane measured from the images is about 0.30 nm and that of the [103] plane was about 0.28 nm. These results are very close to the lattice spacing of the [102] plane (0.305 nm) and of the [103] plane (0.282 nm) of previously reported hexagonal CuS nano structures.

Figure 3:
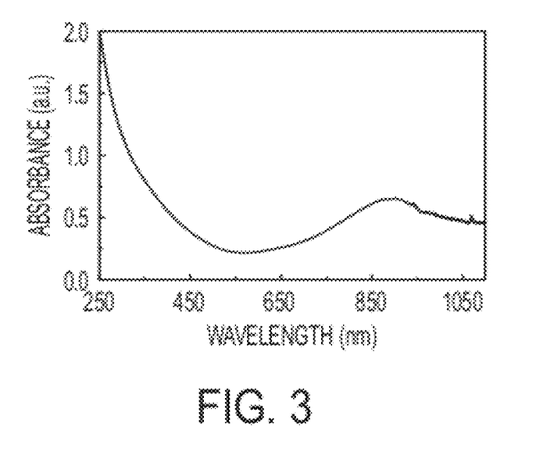
FIG. 3 shows an optical absorption spectrum of CuS nanoparticles.

FIG. 3 shows the optical absorption spectrum of CuS nanoparticles in accordance with an embodiment of the invention. The short-wavelength absorption edged at about 500 nm, which was a significant blue shift from the energy gap of bulk CuS, confirming the effect of quantum size confinement. The sample shows an increased absorption band in the NIR region, with maximum absorption at 900 nm. On the basis of the absorbance measurement, the absorption coefficient value (c) was estimated to be about $2\times10^7$ M$^{-1}$ cm$^{-1}$ at 900 nm. The peak absorption of our sample was assigned to the overlapping d-d transition of $Cu^{2+}$ in a trigonal environment, which was about a 20-nm blue shift, whereas the blue shift of other CuS nanoparticles reported in the literature was about 5 nm in diameter. The observed blue shift in the absorption spectrum of our sample was most likely due to the weakening of the crystal field strength because our nanoparticles were smaller in size than the previously studied CuS nanoparticles. Because of the smaller size of our nanoparticles, fewer ions were coordinated at sites near the surface than in bulk CuS. In addition, interaction with distant neighboring ions is much weaker or nonexistent in smaller CuS nanoparticles compared to that in bulk CuS. Thus, it is expected that the crystal field interaction of these ions is weaker in smaller nanoparticles. As a result, the lowest excited state of the d electrons is up-shifted and the d-d transition is shifted to the blue. There were no shoulders observed at 450 nm, which is a typical absorption peak of $Cu_2S$ phase. These results, along with the XRD and HRTEM results, show the formation of pure and high-quality CuS nanoparticles.

Figure 4:
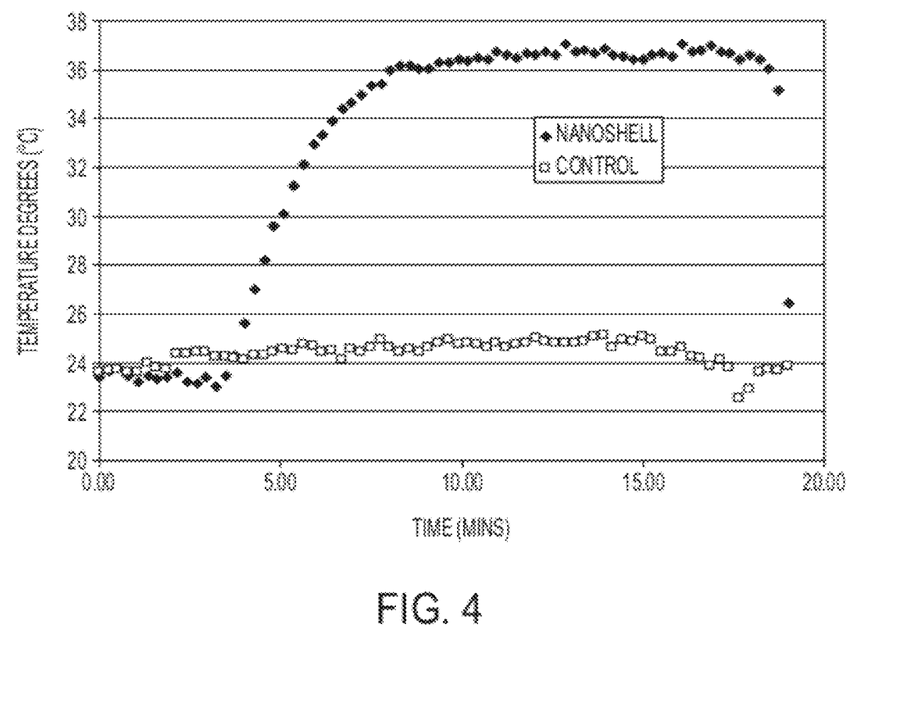
FIG. 4 shows the results of an experiment where temperature was measured over a period of 15 min of exposure to 808-nm NIR light at an output power of 24 W/cm$^2$. The concentration of CuS nanoparticles in water was 770 µM equivalent CuS. Arrows indicate the time points at which the laser power was switched on. Water was used as a control. NP=nanoparticles.

The intense absorption by CuS nanoparticles of the NIR enable their use in PTA therapy. FIG. 4 displays the temperature of an aqueous solution containing CuS nanoparticles as a function of exposure time to a laser beam at 808 nm. The temperature increased 12.7° C. over a period of 5 min at an output power of 24 W/cm$^2$ and a concentration of 770 μM CuS "molecules" (~$1.42\times10^{14}$ particles/mL). Under the same conditions, no change in temperature was observed with pure water (FIG. 4). Thus, the nanoparticles of the invention mediate photothermal effects at 808 nm in the NIR region. Because the absorption of CuS nanoparticles peaks at 900 nm, it is anticipated that the photothermal effect mediated by CuS nanoparticles at the peak absorbance wavelength of 900 nm would be much stronger than that obtained at 808 nm.

Figure 5A:
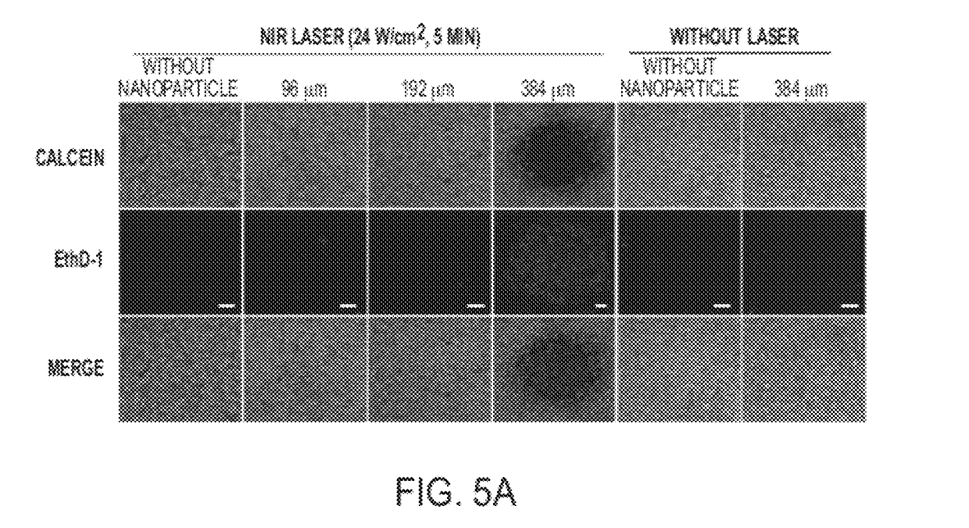
Figure 5B:
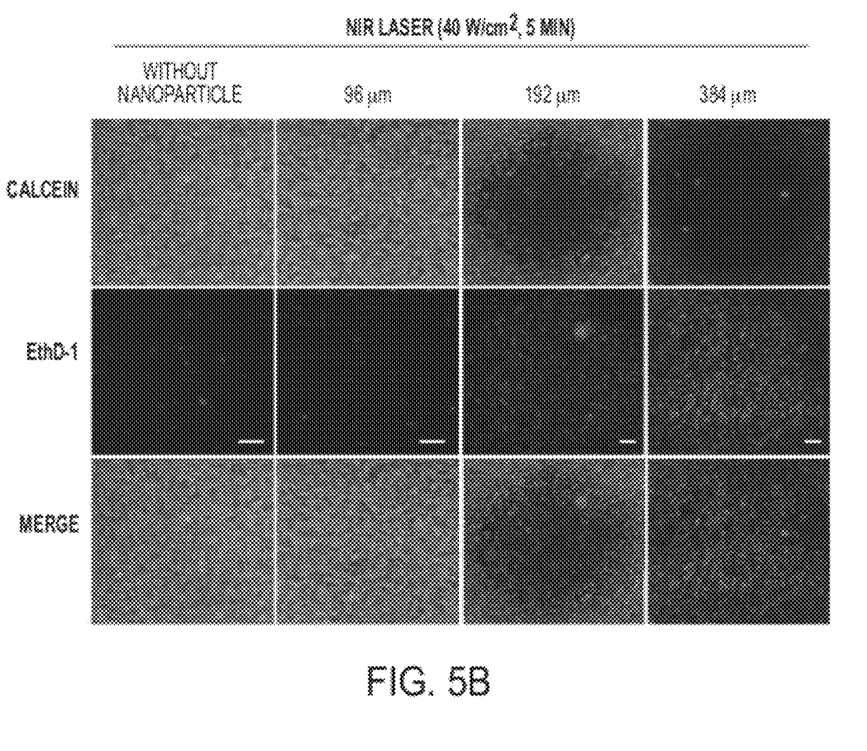
Figure 6:
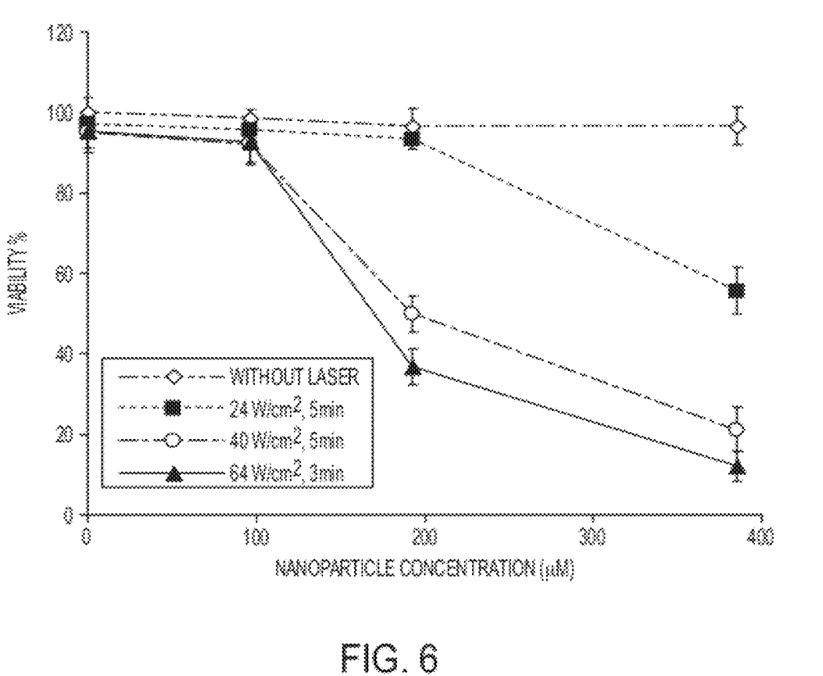
FIG. 6 shows the results of cell viability following treatment with different CuS nanoparticle concentrations and different NIR laser doses. The values are presented as mean±standard deviation from triplicate samples. Asterisks represent a significant difference from the untreated control cells (p<0.05). NP=nanoparticles.

To test the cell killing induced by the photothermal effects of CuS nanoparticles, HeLa cells were incubated with CuS nanoparticles for 2 h. The cells were chosen because near-infrared light can be potentially useful to illuminate cervical cancer and precancerous lesions. The cells were then irradiated with an NIR laser centered at 808 nm. As shown in FIG. 5, 24 h after laser treatment, cells treated with CuS nanoparticles plus an NIR laser experienced substantial cellular death. In fact, at a CuS concentration of 384 μM and an output power of 40 W/cm$^2$, cell death expanded beyond the zone of laser exposure, indicating the spread of heat outside the area of laser irradiation (FIG. 5). No apparent cell death was observed in cells treated with CuS nanoparticles alone or with laser alone. Quantitative analysis of cell viability showed that at the laser power of 24 W/cm$^2$ for 5 min, the percentage of viable cells was 55.6±5.8% when cells were pre-treated with CuS nanoparticles at a concentration of 384 μM CuS. At the same nanoparticle concentration, the cell viability decreased to 21.2±5.6% and 12.2±3.7% when the laser power was increased to 40 W/cm$^2$ for 5 min and 254 W/cm$^2$ for 3 min, respectively. A similar trend was found when the nanoparticle concentration was increased and the laser power was maintained (FIG. 6). These data indicate that the extent of cell death caused by the photothermal effect mediated by CuS nanoparticles is a function of the concentration of the nanoparticles and the output power of the laser used.

Figure 7:
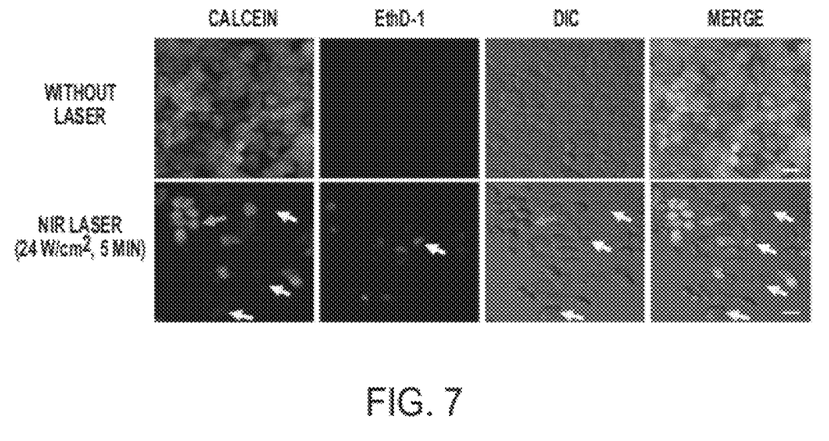
FIG. 7 shows microphotographs of cells incubated with CuS nanoparticles (384 µM CuS) followed by NIR laser irradiation (24 W/cm$^2$, 5 min). Without laser treatment, the cells were viable and polygonal. In contrast, most cells treated with the NIR laser shrank and had spherical morphology. Some cells lost viability, as evidenced by calcein-negative staining (grey arrows). Others lost membrane integrity, as indicated by positive staining with EthD-1 (white arrows). DIC, differential interference contrast. Bar=20 µm.

Morphologically, the untreated HeLa cells were polygonal, and few cells were stained red with ethidium homodimer-1 (EthD-1). However, after treatment with CuS nanoparticles (384 μM CuS) and the NIR laser, many cells that stained positive with calcein (green) became more rounded in shape, possibly as a result of the condensation of skeletal proteins. Some cells lost their viability, as indicated by calcein-negative staining (FIG. 7). The rest of the cells stained positive with EthD-1, which indicates loss of cellular membrane integrity (FIG. 7).

Figure 8:
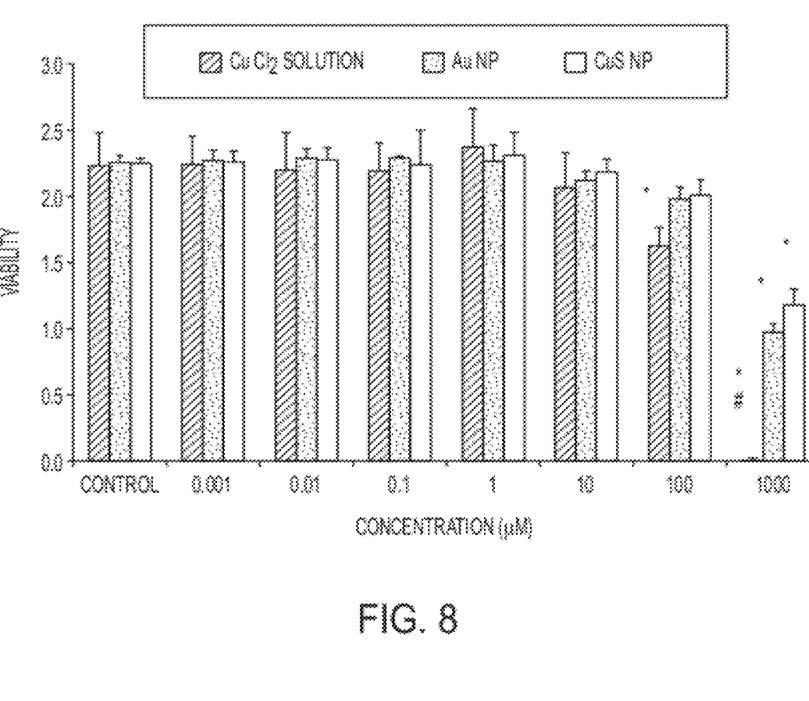
FIG. 8 shows the cytotoxicity of CuS nanoparticles in HEK293 cells. (A) The cells were incubated in culture medium containing nanoparticles at concentrations ranging from 1 nM to 1 mM for 48 h. CuCl$_2$ solution and 20-nm gold nanoparticles were included in the study. Cell viability is expressed as the absorbance at 430 nm. Control: untreated cells. Data represent mean±standard deviation. *p<0.05 compared to untreated control. #p<0.05 compared to CuS nanoparticles (B).

The cytotoxicity of CuS nanoparticles in human embryonic kidney 293 cells (HEK293) are compared to that of 20-nm gold nanoparticles, which are well accepted as a biocompatible nanomaterial (FIG. 8). Both CuS and gold nanoparticles (20 nm) had no cytotoxic effect on the cells at concentrations up to 100 μM after 48 h of incubation. At the highest concentration tested (1 mM), both nanoparticles caused a significant decrease in cell viability. The aqueous solution of $CuCl_2$, which was used for the preparation of CuS nanoparticles, was significantly more cytotoxic than its corresponding CuS nanoparticles at the same equivalent concentration of CuS at >100 μM. Almost all cells were dead after treatment with the aqueous solution of $CuCl_2$ at 1 mM. These data suggest that CuS nanoparticles have a cytotoxicity profile comparable to that of gold nanoparticles.

The nanoparticles of the claimed invention offer several advantages over prior art nanostructures. First, copper-based nanoparticles are less expensive than previously used gold nanoparticles. Second, the NIR absorption in CuS originates from the d-d transition of $Cu^{2+}$ ions, whereas the NIR absorption in gold nanostructures is from the surface plasmon resonance. The former is an intrinsic property in which the absorption peak is primarily determined by the composition and the crystal structure of the nanoparticles. Therefore, unlike gold nanostructures, the peak absorption for nanoparticles of the claimed invention does not vary significantly with size, shape, structure, or the dielectric constant of the surrounding matrix. Third, special structural features such as core-shell nanoshells or nanorods with aspect ratios greater than one are necessary in order for gold nanostructures to exhibit surface plasmon absorption in the NIR region. The protocols for making these special nanostructures are more complicated than the simple recipe for making CuS nanoparticles in aqueous solution. Lastly, the nanoparticles having a size of about 3 nm may have more favorable pharmacokinetic properties for targeted delivery after systemic administration than that of gold nanostructures displaying surface plasmon absorption in the NIR region. To date, the smallest gold nanostructures having NIR absorption was ~40 nm in diameter. The smaller CuS nanoparticles may have a better chance of reaching their targets and being cleared from the body through the renal system.

The foregoing detailed description is given primarily for clarity of understanding and no unnecessary limitations are to be understood therefrom for modifications that can be made by those skilled in the art upon reading this disclosure and may be made without departing from the spirit of the invention.

What is claimed is:

1. A method for the removal of cancer cells, the method comprising the steps of: (a) providing optically heatable nanoparticles having diameters of about 3 nm, wherein the optically heatable nanoparticles have the formula $Cu_xS_y$, (0<x<1, 0<y<1); (b) delivering the nanoparticles to target cancer cells; (c) optically heating the nanoparticles located at the target cancer cells for a period of time ranging from 3-5 minutes, whereby optically heating the nanoparticles results in thermal ablation of at least a portion of the target cancer cells; (d) increasing the temperature of the cancer cells; and (e) decreasing the viability of the cancer cells by at least 40%.

2. The method of claim 1, wherein the nanoparticles are optically heated with light having a wavelength in the range of 700-1100 nm.

* * * * *